(12) United States Patent
Wood

(10) Patent No.: US 11,969,571 B2
(45) Date of Patent: *Apr. 30, 2024

(54) MULTI-USE DISINFECTING CAP

(71) Applicant: Barry Edward Wood, Georgiana, AL (US)

(72) Inventor: Barry Edward Wood, Georgiana, AL (US)

(*) Notice: Subject to any disclaimer, the term of this patent is extended or adjusted under 35 U.S.C. 154(b) by 0 days.

This patent is subject to a terminal disclaimer.

(21) Appl. No.: 18/078,933

(22) Filed: Dec. 10, 2022

(65) Prior Publication Data

US 2023/0109339 A1 Apr. 6, 2023

Related U.S. Application Data

(63) Continuation of application No. 16/560,927, filed on Sep. 4, 2019, now Pat. No. 11,547,844.

(Continued)

(51) Int. Cl.
| | |
|---|---|
| *A61L 2/00* | (2006.01) |
| *A01N 31/02* | (2006.01) |
| *A01N 47/44* | (2006.01) |
| *A61L 2/18* | (2006.01) |
| *A61L 2/26* | (2006.01) |
| *A61M 5/14* | (2006.01) |
| *A61M 39/02* | (2006.01) |
| *A61M 39/16* | (2006.01) |
| *A61M 39/18* | (2006.01) |
| *A61M 39/10* | (2006.01) |

(52) U.S. Cl.
CPC .............. *A61M 39/18* (2013.01); *A01N 31/02* (2013.01); *A01N 47/44* (2013.01); *A61L 2/18* (2013.01); *A61L 2/26* (2013.01); *A61M 5/1413* (2013.01); *A61M 39/0208* (2013.01); *A61M 39/162* (2013.01); *A61M 39/165* (2013.01); *A61L 2202/122* (2013.01); *A61L 2202/24* (2013.01); *A61M 2039/1033* (2013.01); *A61M 2205/583* (2013.01)

(58) Field of Classification Search
CPC ........ A61L 2/00; A61L 2/18; A61L 2202/121; A61L 2202/122; A61L 2202/123; A61L 2202/24; A61M 39/18; A61M 39/165; A01N 47/44
USPC .......... 422/28, 292, 302; 604/283, 411, 905; 366/165, 264
See application file for complete search history.

(56) References Cited

U.S. PATENT DOCUMENTS

| | | | | |
|---|---|---|---|---|
| 5,190,534 | A * | 3/1993 | Kendell | B08B 3/048 |
| | | | | 604/29 |
| 5,326,166 | A * | 7/1994 | Walthall | B01F 25/10 |
| | | | | 239/10 |
| 11,547,844 | B2 * | 1/2023 | Wood | A61M 39/0208 |

* cited by examiner

*Primary Examiner* — Monzer R Chorbaji
(74) *Attorney, Agent, or Firm* — Sandra L Layer

(57) ABSTRACT

A multi-use disinfecting cap and method for disinfection and protection of a needleless IV injection port. The disinfecting cap has an upper chamber which contains a sterilizing solution and a low chamber which connects to a needleless IV injection port. The fluid can be manipulated to flow between the two chambers. When in use the cap protects and disinfects a needleless IV injection port when exposed prior to injecting medication into the needleless port and continues to disinfect and protect prior for any subsequent exposures. The cap is re-usable and provides a clear indication of the disinfecting solution and a datable top surface. The multi-use disinfecting cap may be removably clipped to the IV tubing and is shaped to prevent accidental rolling away if dropped.

16 Claims, 8 Drawing Sheets

Related U.S. Application Data

(60) Provisional application No. 62/727,266, filed on Sep. 5, 2018.

SECTION A-A

MULTI-USE DISINFECTING CAP

RELATED APPLICATION

The present patent application is a continuation-in-part of U.S. patent application Ser. No. 16/560,927 entitled "MULTI-USE DISINFECTING CAP AND METHOD" filed on Sep. 4, 2019 which claims priority to the corresponding provisional patent application Ser. No. 62/727,266, entitled "MULTI-USE DISINFECTING CAP" filed on Sep. 5, 2018, the subject matter of which applications are incorporated in entirety herein by reference.

BACKGROUND OF THE INVENTION

The present invention relates to a multi-use disinfecting cap and more particularly pertains to a multi-use cap for disinfection and protection of a needleless IV injection.

DESCRIPTION OF THE PRIOR ART

The use of disinfecting caps is known in the prior art. More specifically, disinfecting caps previously devised and utilized for the purpose of disinfecting the surface of a needleless IV injection port are known to consist basically of familiar, expected, and obvious structural configurations, notwithstanding the myriad of designs encompassed by the crowded prior art which has been developed for the fulfillment of countless objectives and requirements.

While these devices fulfill their respective, particular objectives and requirements, the aforementioned patents do not describe multi-use disinfecting cap and method that allows a multi-use cap for disinfection and protection of a needleless IV injection port.

In this respect, the multi-use disinfecting cap according to the present invention substantially departs from the conventional concepts and designs of the prior art, and in doing so provides an apparatus primarily developed for the purpose of a multi-use cap for disinfection and protection of a needleless IV injection.

Therefore, it can be appreciated that there exists a continuing need for a new and improved multi-use disinfecting cap which can be used for a multi-use cap for disinfection and protection of a needleless IV injection port. In this regard, the present invention substantially fulfills this need.

SUMMARY OF THE INVENTION

In view of the foregoing disadvantages inherent in the known types of disinfecting caps now present in the prior art, the present invention provides an improved multi-use disinfecting cap. As such, the general purpose of the present invention, which will be described subsequently in greater detail, is to provide a new and improved multi-use disinfecting cap which has all the advantages of the prior art and none of the disadvantages.

To attain this, for a broad perspective, the present invention essentially comprises a disinfecting cap having an upper chamber and a lower chamber. The upper chamber having an upper cylindrical section. The top of the upper cylindrical section sealed with a planar surface. The upper chamber having a lower conical section forming a funnel and in fluid communication with the lower chamber. The upper chamber being transparent to view the tinted disinfecting solution contained in the upper chamber. The lower chamber being transparent to view the tinted disinfecting solution when present in the lower chamber. The lower chamber being cylindrical having an upper end formed with an annular ridge projecting radially inward in proximity to the lower conical section of the upper chamber. The lower chamber having an interior surface formed with female threads. The lower extent of the lower chamber adapted to receive a needleless IV connector port. The lower chamber having an open lower end. A removable seal covering the open lower end of the lower chamber.

One optional feature of the disinfecting cap is an upper planar surface for accepting indicia and sealing the top.

Another optional feature is a retaining clip formed on the upper edge of the upper chamber having a slot formed to connect the disinfecting cap to an IV line constricting the line and for handling purposes to keep the cap close. The slot is configured with an enlarged portion to connect to the IV line without constricting the tube and a narrow portion to constrict the IV line when connected.

An additional optional feature is a sponge having one end contained in the lower chamber to facilitate movement of the disinfecting solution between the upper chamber and a connected needleless IV port.

Another feature is a vent formed in the top of the cap to equalize pressure between the upper and lower chambers allowing the disinfecting solution to flow freely between the two chambers.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved multi-use disinfecting cap which has all of the advantages of the prior art disinfecting caps and none of the disadvantages.

It is another object of the present invention to provide a new and improved multi-use disinfecting cap which may be easily and efficiently manufactured and marketed.

It is a further object of the present invention to provide a new and improved multi-use disinfecting cap which is of durable and reliable constructions.

An even further object of the present invention is to provide a new and improved multi-use disinfecting cap which is susceptible of a low cost of manufacture with regard to both materials and labor, and which accordingly is then susceptible of low prices of sale to the consuming public, thereby making such multi-use disinfecting cap economically available to the buying public.

Lastly, it is an object of the present invention to provide a multi-use disinfecting cap for safe multiple use protection and disinfecting of needleless IV ports before, between and after exposures of the needless IV connecting port for injections of medicine.

These together with other objects of the invention, along with the various features of novelty which characterize the invention, are pointed out with particularity in the claims annexed to and forming a part of this disclosure.

For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

The same reference numerals refer to the same parts throughout the various Figures.

DESCRIPTION OF THE PREFERRED EMBODIMENT

Figure 1:
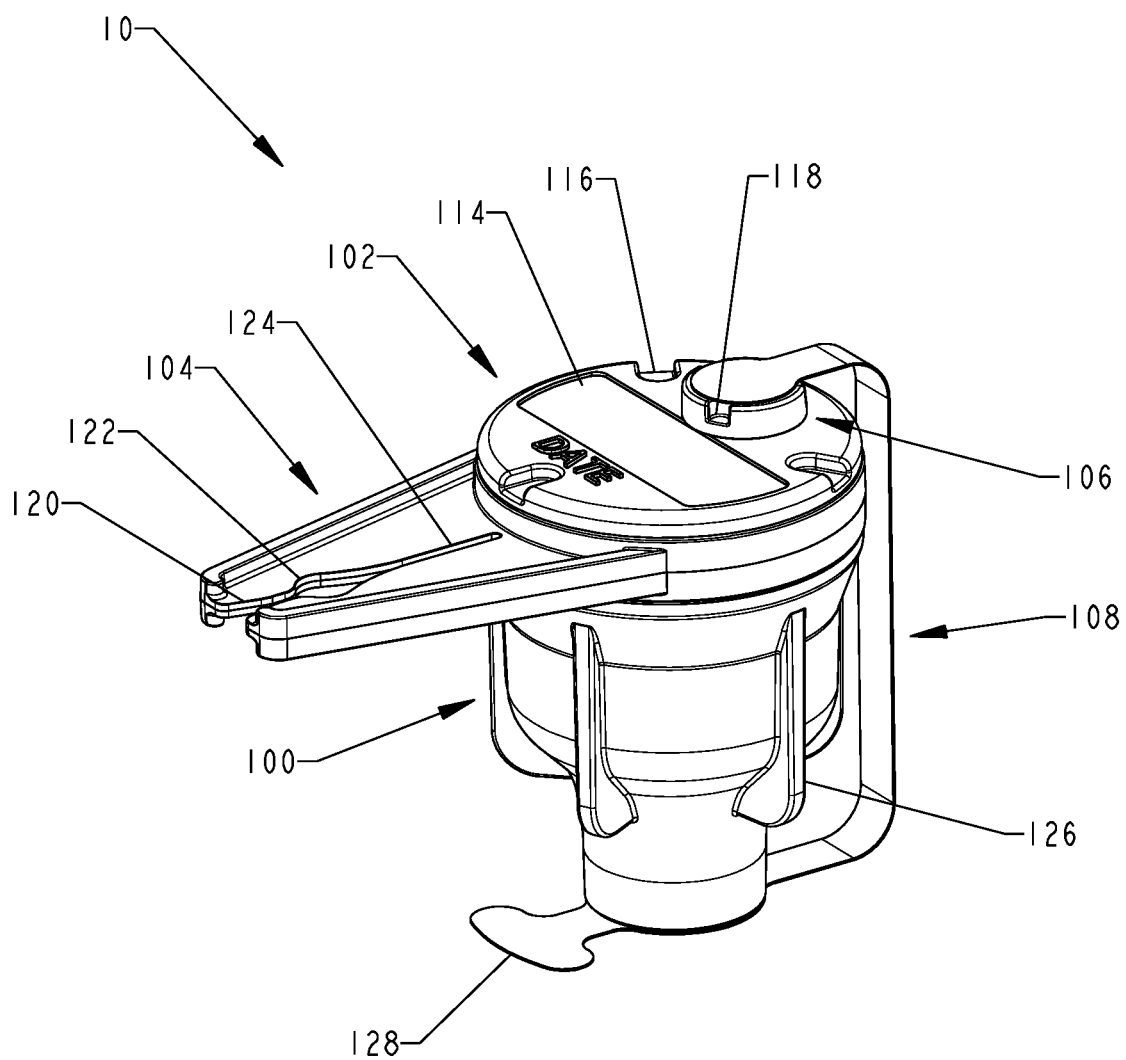
FIG. 1 is a front perspective view of a disinfecting cap constructed in accordance with the principles of the present invention shown as used for connecting to a needleless IV port.
Figure 2:
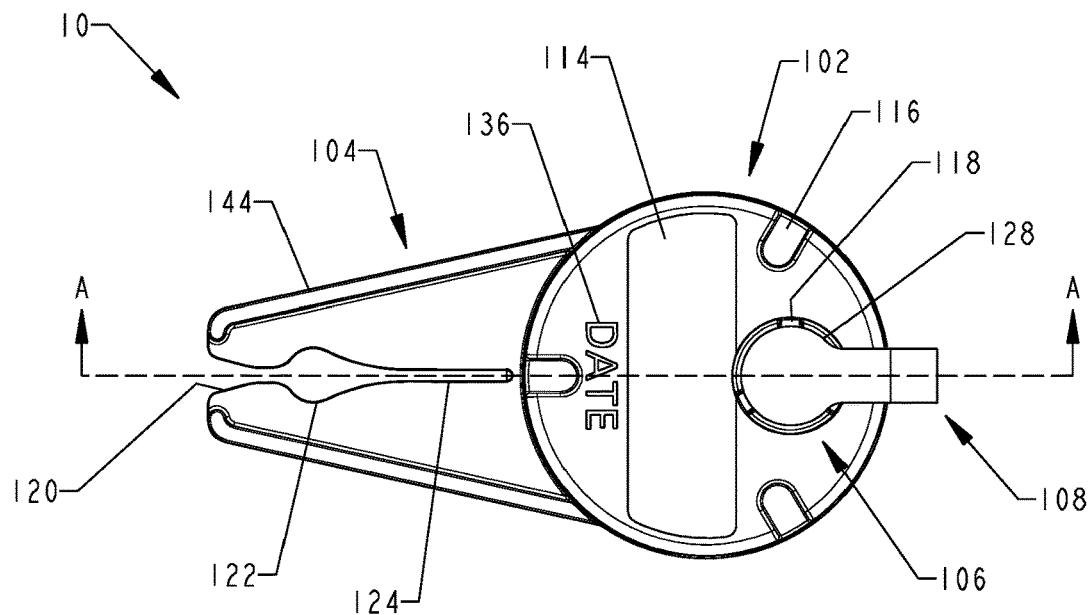
FIG. 2 is a top view of a disinfecting cap constructed in accordance with the principles of the present invention and having a slot for connecting to an IV tube.
Figure 3:
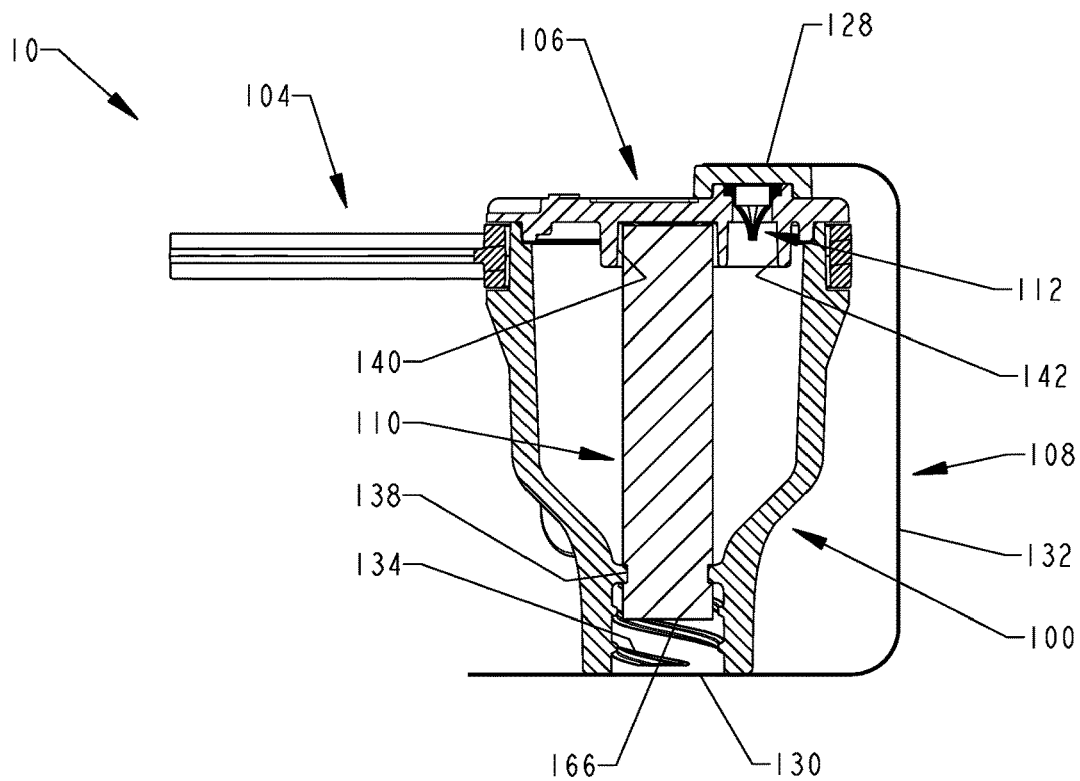
FIG. 3 is a cross-sectional side view of the present invention taken along lines A-A of FIG. 2.

With reference now to the drawings, and in particular to FIG. 1 thereof, the preferred embodiment of the new and improved multi-use disinfecting cap and method embodying the principles and concepts of the present invention and generally designated by the reference numeral 10 will be described.

The present invention, the multi-use disinfecting cap 10 is comprised of a plurality of components. Such components are individually configured and correlated with respect to each other so as to attain the desired objective. In their broadest context such include an upper chamber and a lower chamber. The upper chamber transparent and in fluid communication with the lower chamber. The top of the upper chamber sealed with a planar surface. The upper chamber is filled with disinfecting solution, such as isopropyl alcohol or chlorhexidine. The transparent lower chamber is configured to couple to a needleless IV port connector. In this broad context, first provided is an upper chamber and a lower chamber. The upper chamber sealed on top with a cap 102 having a planar surface 114 capable of receiving indicia and in fluid communication with the lower chamber. The lower portion of the upper chamber having a lower conical section. A disinfecting solution is contained in the upper chamber. Both the upper and lower chambers are transparent. The lower chamber has an upper end with one or more annular ridges 138 projecting inward in proximity to the conical section of the upper chamber. The lower extent of the lower chamber is adapted to receive a needleless IV connector port 148. The lower chamber having an open lower end 134 and a removable seal 130 covering the open end 134 of the lower chamber. Such components are individually configured and correlated with respect to each other so as to attain the desired objective.

Figure 4:
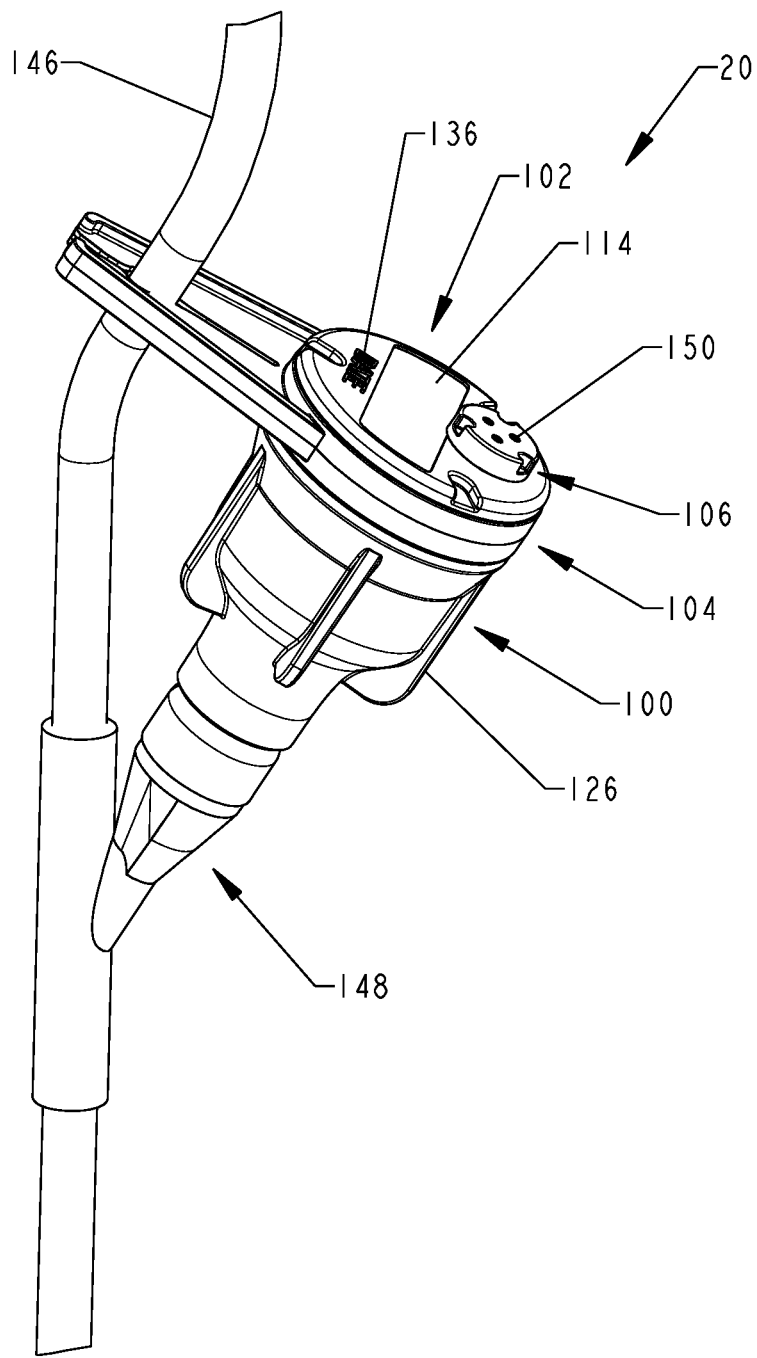
FIG. 4 is a perspective view of a disinfecting cap constructed in accordance with the principles of the present invention shown in use connected to a needleless IV port.
Figure 5:
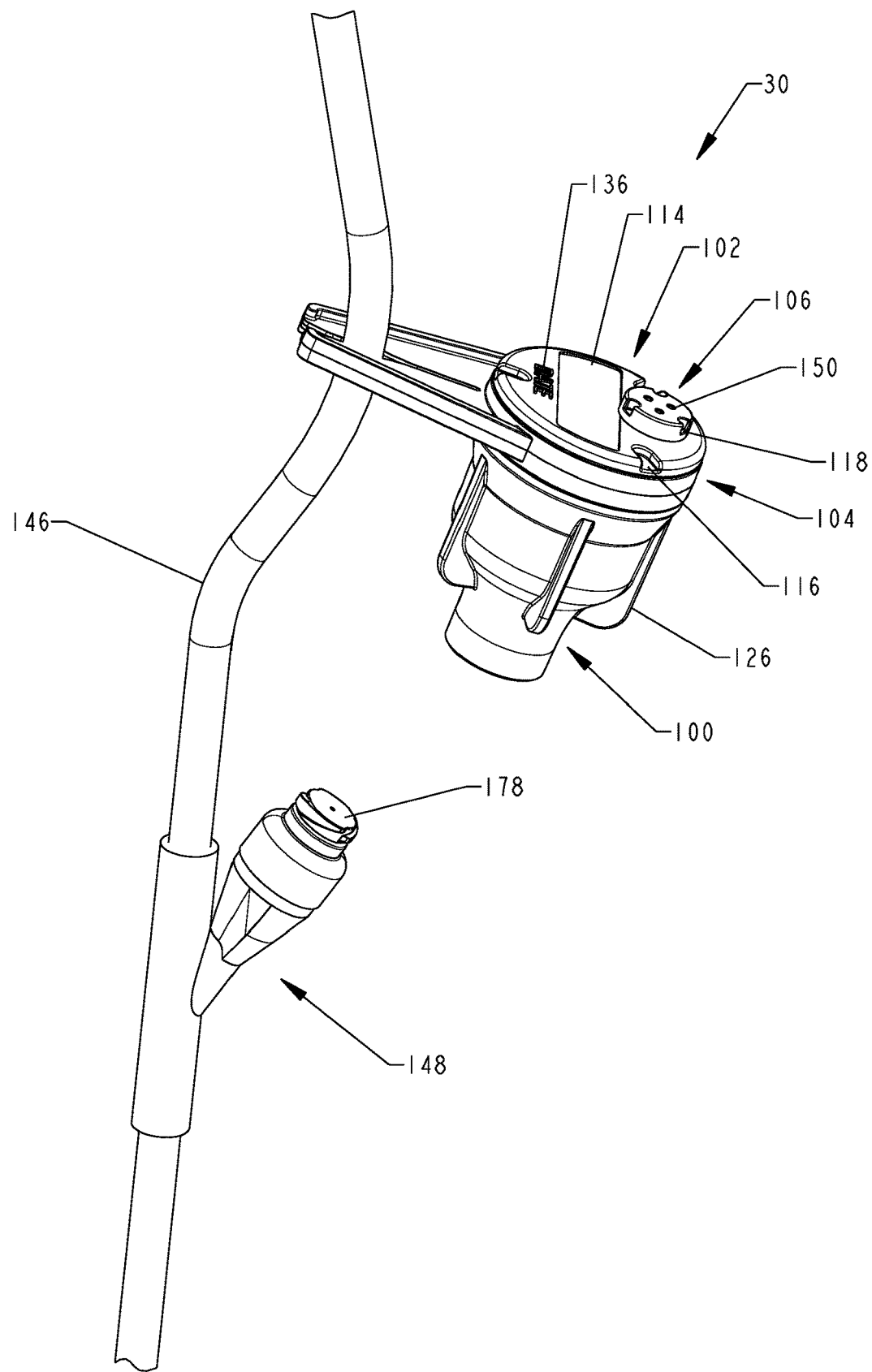
FIG. 5 is a side perspective view of a disinfecting cap constructed in accordance with the principles of the present invention shown as used for connecting to a needleless IV port attached to an IV tube and removed from the needleless port.
Figure 6:
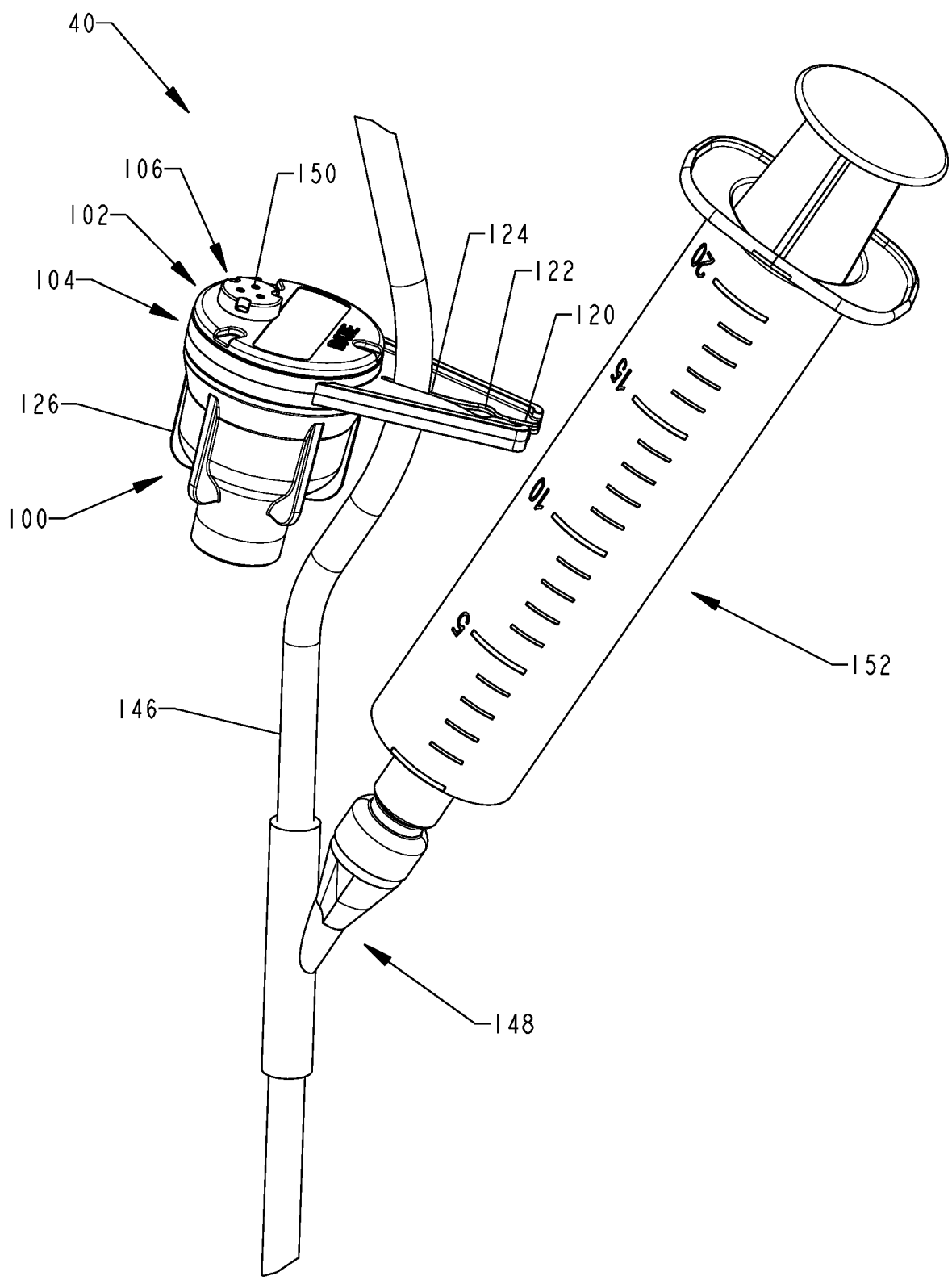
FIG. 6 is a perspective view of a disinfecting cap in use connected to an IV tube and removed from a needleless IV port while fluid is injected into the associated needleless IV port.
Figure 7:
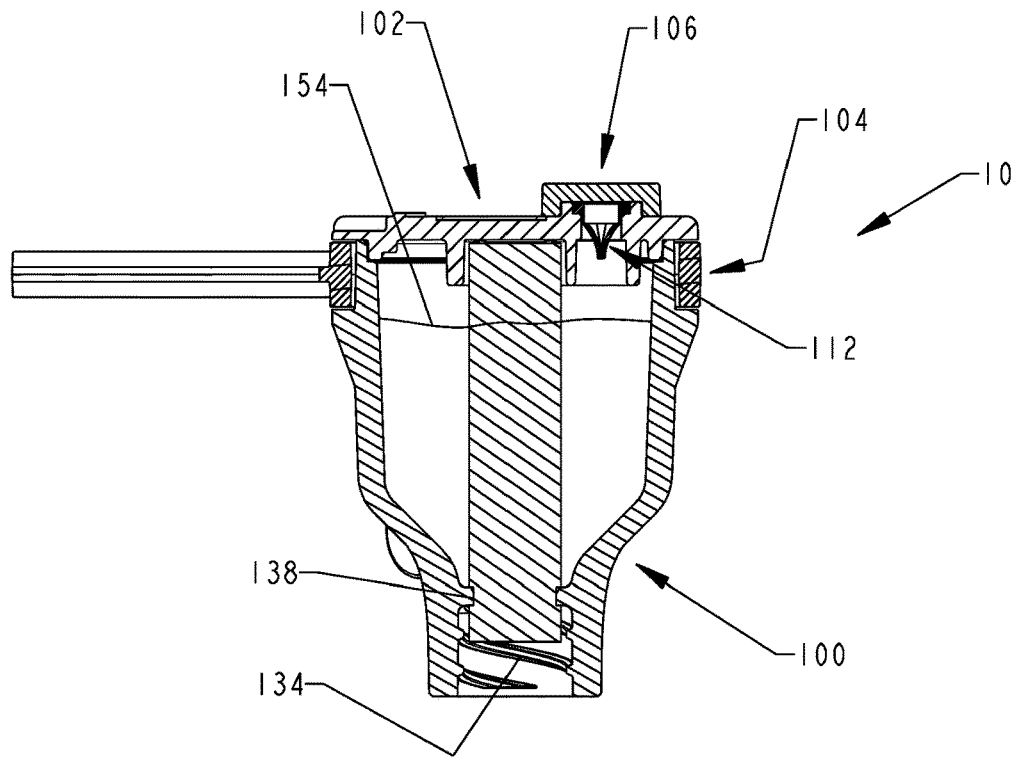
FIG. 7 is a cross-sectional side view of a disinfecting cap constructed in accordance with the principles of the present invention.
Figure 8:
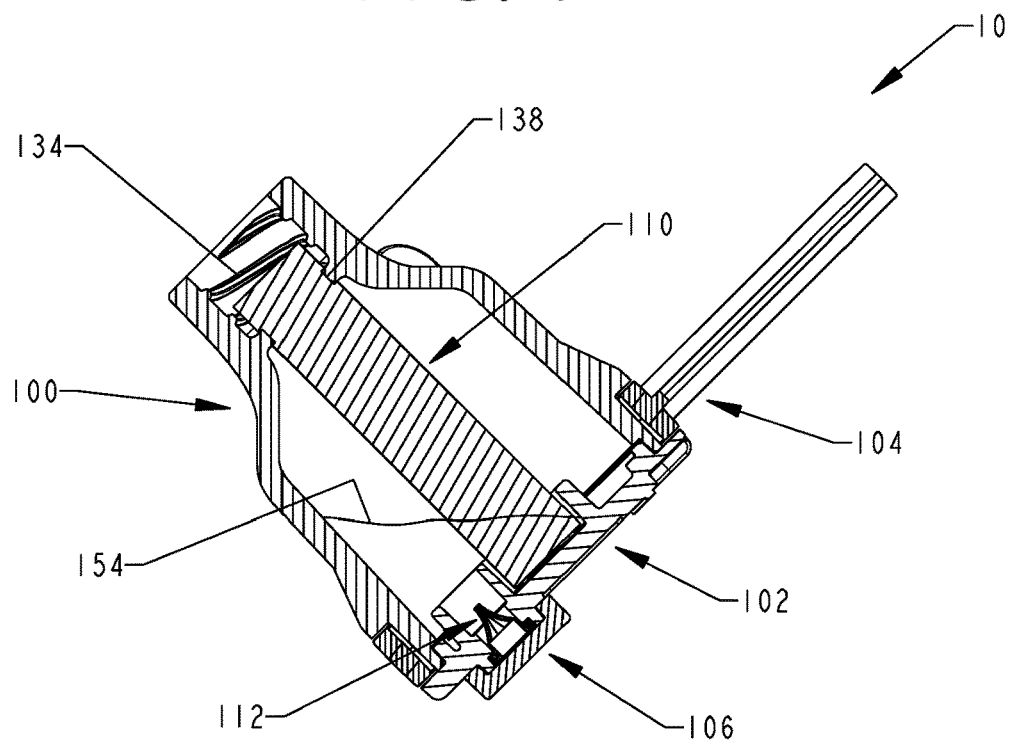
FIG. 8 is a cross-sectional view of a disinfection cap inverted and including wicking material extending from the lower chamber to the upper chamber for the movement of disinfecting fluid.
Figure 9:
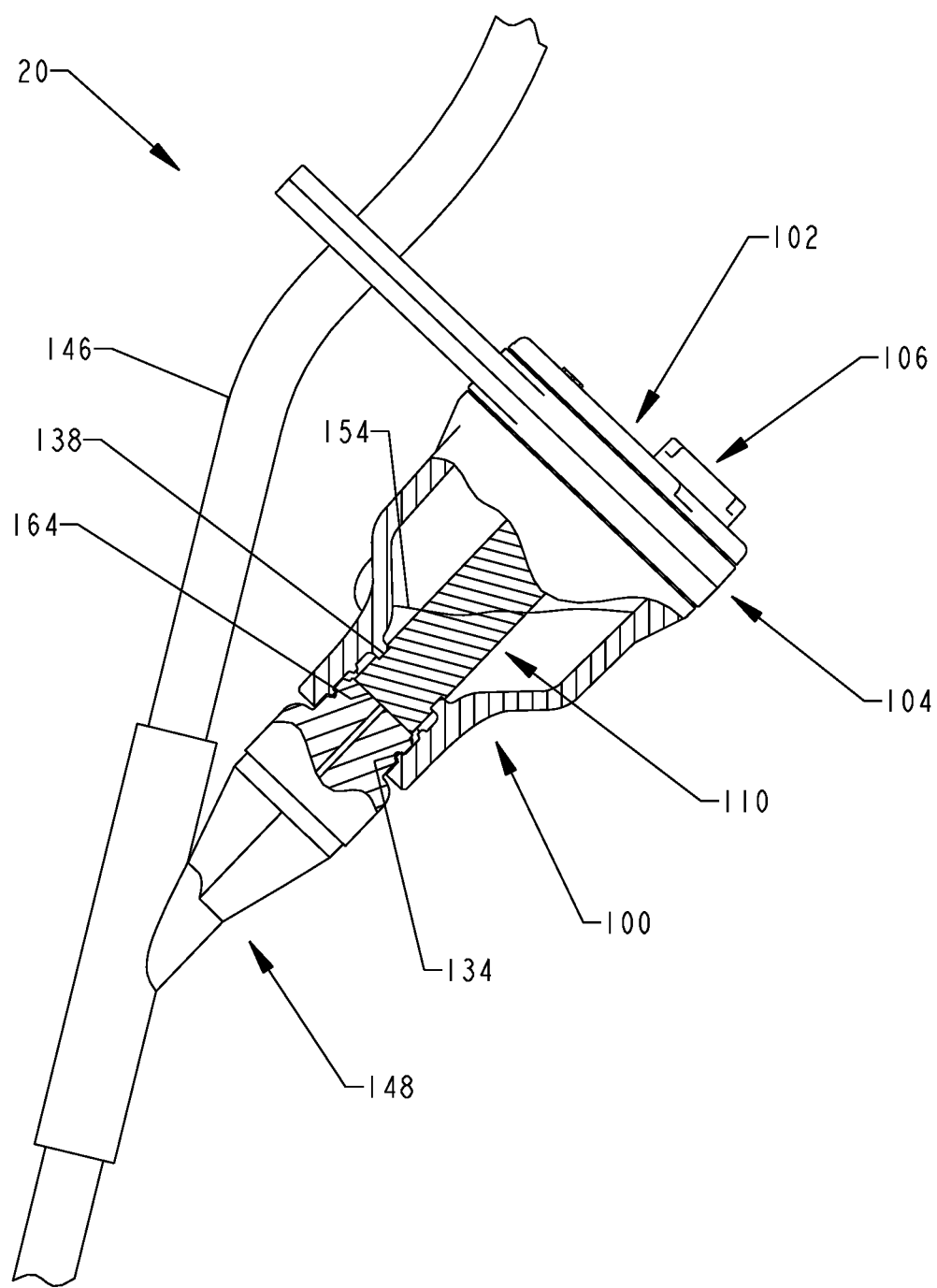
FIG. 9 is a cross-sectional view of a disinfecting cap in use, connected to a needleless IV port.
Figure 10:
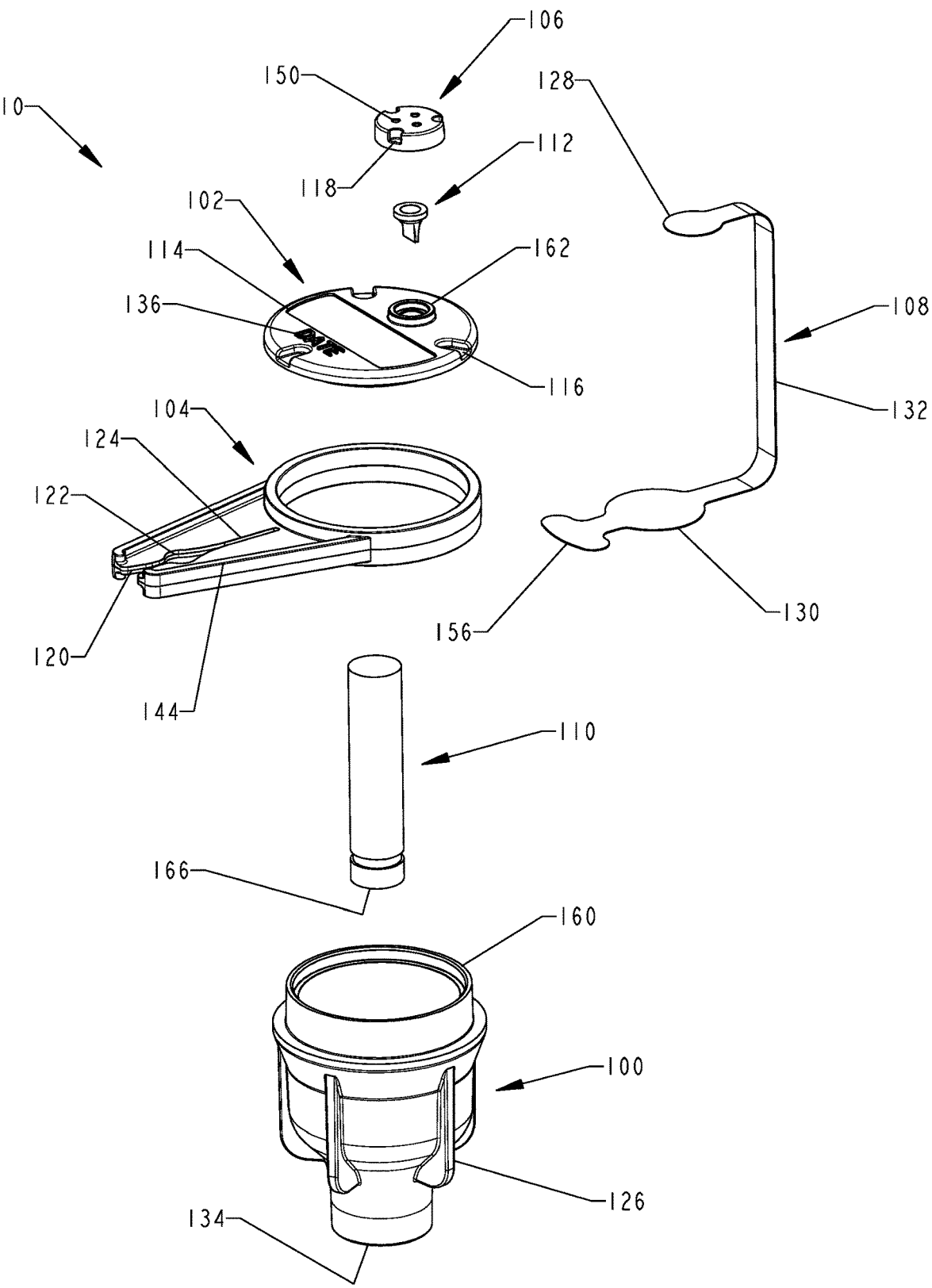
FIG. 10 is an exploded view of a disinfecting cap constructed in accordance with the principles of the present invention.

In the preferred embodiment of the multi-use disinfecting cap, designated by reference numeral 10 and shown in FIGS. 1-10, first provided is a disinfecting cap configured for use with a needless IV port. FIGS. 4, 5 and 6 show the disinfecting cap in various stages of use, attached to an IV tube and needless port 20 (FIG. 4), attached to an IV tube and removed from the needleless port 30 (FIG. 5), and attached to the IV tube, removed from the needleless port and a syringe 152 attached to the needleless port 40 (FIG. 6). The cap comprising a reservoir 100 having an upper chamber and a lower chamber. The upper chamber having a closed top and an open lower end. The top of the upper chamber is sealed with an upper seal consisting of a planar surface for receiving written indicia 114, a label 136 is adjacent to the planar surface. The upper chamber being transparent. The upper chamber having an upper cylindrical section with a diameter of 0.83 inches plus or minus 10 percent. The upper chamber having a lower conical section forming a funnel in fluid communication with the lower chamber with an axial opening 134 on the lower end. The upper chamber is filled with disinfecting solution, the disinfecting solution taken from a class of disinfectants including isopropyl alcohol and chlorhexidine and in the preferred embodiment the disinfecting fluid is tinted.

The lower chamber is below and in fluid connection with the upper chamber. The lower chamber is cylindrical and transparent. The lower chamber having a second diameter of 0.36 inches plus or minus 10 percent and a height of 0.425 inches plus or minus 10 percent. The lower chamber is formed with an annular ridge 138 projecting inward in proximity to the lower conical section of the upper chamber. The lower extent of the lower chamber having female threads adapted to receive a needleless IV connector port 148 such as a female luer connector port. The lower chamber is in fluid connection with the top 178 of the needleless IV connector port 148 (needleless IV connector port in the form of a female luer connecter port is shown in FIGS. 4, 5, 6 and 9 for reference only) when coupled. A removable lower seal 130 covers the lower edge 134 of the lower chamber.

The removable lower seal 130 of the lower edge is detachable for use before removably connecting to the needleless IV connector port 148 allowing disinfecting fluid to contact the upper surface of the needleless IV connector port.

In one embodiment, a vent 106 is formed in the closed top of the upper chamber for pressure equalization. The vent is comprised of one or more openings 150 covered by a vent cap or an upper seal 128. The upper seal or vent cap is removed when the disinfecting cap is attached to the needleless IV connector port to equalize pressure within the disinfecting cap allowing the disinfecting fluid to flow freely between the upper and lower chambers to contact the upper surface of the needleless IV connector port.

In another alternate embodiment, the vent formed in the closed top is a duckbill valve 112.

Optionally a single foil 108 having and upper seal 128 and a lower seal 130 with a connecting center strip 132 can be used to seal both the vent opening and the bottom opening of the lower chamber.

A retaining clip 104 extends radially outward from the top of the upper cylindrical section for connecting to an IV tube. The retaining clip is formed in a triangular configuration having a radial slot 124 extending inward from the tip 120 for attaching to and constricting the IV tube when disconnecting the disinfecting cap to access the needleless IV port. The slot 124 is formed with an enlarged circular opening 122 for allowing for unrestricting attachment to the IV tube. A raised edge 144 extending along the outer perimeter of the retaining clip provides added rigidity.

In still another alternate embodiment a wicking material 110 such as a sponge is located in the lower chamber and extends into the bottom of the upper chamber to facilitate movement of the disinfecting solution from the upper chamber to the top of the needleless IV injection port. In the preferred embodiment the wicking material is formed as a cylindrical sponge that extends from the lower chamber to the top of the upper chamber and has an external diameter equal to the interior diameter of the annular ridge of the lower chamber, the annular ridge holding the lower end of the sponge in place and a secondary retaining ridge 140 extending downward from the interior of the top of the upper chamber having a diameter equal to the diameter of the annular ridge to secure the upper portion of the sponge in place.

One optional feature of the disinfecting cap includes finger grips projecting outward from the upper chamber to aid in the removal of the cap from the needleless IV connector port. An additional optional feature includes spin welding tool engagement slots 116, 118 on the outer edge of the top of the upper chamber and the top of the vent.

The disinfecting cap is a multiuse cap for disinfecting and protecting a needless IV injection port. The transparent chambers and tinted disinfecting solution allow for multiple use by providing a visual indication of useful solution. The disinfecting cap is a small dual chambered device comprised of a larger chamber that acts as a reservoir and a smaller chamber that acts to keep alcohol in contact with the needleless IV port. The wicking material keeps the solution in contact with the port. A small annular ridge separates the two chambers holding the wicking material in place and providing a conduit to cause the disinfecting solution to be drawn from the larger chamber if the device is turned upside down, keeping the fluid in contact with the top of the needless IV injection port. The larger chamber is tapered to facilitate flow into the smaller chamber. Once the solution flows into the smaller chamber it will remain in contact with the top of the needleless IV injection port (luer valve) thus sterilizing the port. The top of the larger upper chamber may be written on to allow for dating when first connected to the IV tubing. The seal on the bottom of the smaller lower chamber is removable to provide access to the solution when connected to the needleless IV injection port (luer valve). When the seal is removed from the vent in the top of the larger chamber, the vent prevents the vacuum from inhibiting the solution from flowing from the larger chamber to the smaller chamber. The visibility of the tinted solution within the chambers allows nurses and practitioners to easily see that the disinfecting solution is in contact with the port prior to removing for access and reconnecting following injection making the cap ideal for multiuse. The small slot in the top of the cap can be used to secure the cap to the IV tubing both to prevent loss and to eliminate the need for a separate IV tubing roller clamp for preventing back-flow while injecting medication into the exposed port. The angular oval shape of the top flange also prevents rolling in the event the cap is dropped. All of these features result in a device that enhances workflow rather than impeding it. As a nurse anesthetist I constantly access the port during a case. Other devices require constant replacement in order to maintain the proper level of disinfection. In addition to clear indication of the disinfecting solution and datable aging this cap has additional feature to keep it close by clipping to the IV tubing and being shaped to prevent accidental rolling away.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A disinfecting cap, the disinfecting cap having an upper chamber and a lower chamber, the upper chamber having an upper cylindrical section, the upper cylindrical section having a top, the top of the upper cylindrical section sealed with a planar surface, the planar surface having an exterior top and an interior bottom, the upper chamber having a lower conical section, the lower conical section forming a funnel, the lower conical section in fluid communication with the lower chamber, a disinfecting solution contained in the upper chamber, the lower chamber being cylindrical, the lower chamber having an upper end, the lower chamber having an interior surface, the interior surface of the lower extent of the lower chamber being formed with female threads, the lower extent of the lower chamber adapted to receive a needleless IV connector port, the lower chamber having a lower end, the lower end of the lower chamber being open, a removable seal covering the open end of the lower end of the lower chamber.

2. The disinfecting cap of claim 1 further comprising an annular ridge projecting radially inward from the lower chamber in proximity to the lower conical section of the upper chamber, the annular ridge having an interior diameter.

3. The disinfecting cap of claim 2 wherein the wicking material is formed as a cylindrical sponge extending from the bottom of the lower chamber to the top of the upper chamber, the cylindrical sponge having an external diameter equal to the interior diameter of the annular ridge of the lower chamber, the annular ridge holding the lower end of the sponge in place, a secondary retaining ridge extends downward from the interior bottom of the planar surface of the top of the upper chamber having a diameter equal to the interior diameter of the annular ridge.

4. The disinfecting cap of claim 1 wherein the disinfecting solution is taken from a class of disinfecting solutions including isopropyl alcohol and chlorhexidine.

5. The disinfecting cap of claim 1 wherein the disinfecting solution is tinted.

6. The disinfecting cap of claim 1 wherein the upper and lower chambers are transparent.

7. The disinfecting cap of claim 1 in which the top of the upper cylindrical section is formed with a retaining clip extending radially outward from the top of the upper cylindrical section for connecting to an IV tube, the retaining clip formed in a triangular configuration having a base and a tip, the base adjacent to the top of the upper cylindrical section, a radial slot extending inward from the tip.

8. The disinfecting cap of claim 7 wherein the slot is formed with an enlarged circular opening.

9. The disinfecting cap of claim 1 wherein the upper planar surface is capable of receiving indicia.

10. The disinfecting cap of claim 1 further comprising a wicking material contained in the lower chamber.

11. The disinfecting cap of claim 1 further comprising a wicking material extending from the lower chamber into the upper chamber.

12. The disinfecting cap of claim 11 wherein the wicking material is a sponge formed in a cylindrical configuration.

13. The disinfecting cap of claim 1 wherein the planar surface of the top of the upper cylindrical section further comprises a vent.

14. The disinfection cap of claim 13 wherein the vent is a duckbill valve.

15. The disinfecting cap of claim 14 wherein the vent is comprised of one or more holes in the top of the upper cylindrical section.

16. A disinfecting cap configured for use for use with a needless IV port, the disinfecting cap comprising an upper chamber and a lower chamber, the upper chamber having an upper cylindrical section, the upper cylindrical section having a top, the top of the upper cylindrical section sealed with a planar surface, the planar surface having an exterior top and an interior bottom, the top of the upper cylindrical section formed with a retaining clip extending radially outward from the top of the upper cylindrical section for connecting to an IV tube, the retaining clip formed in a triangular configuration having a base and a tip, the base adjacent to the top of the upper cylindrical section, a radial slot extending inward from the tip, the slot formed with an enlarged circular opening;

the upper chamber having a lower conical section, the lower conical section forming a funnel, the lower conical section in fluid communication with the lower chamber, the upper chamber being transparent, the upper chamber filled with a tinted disinfecting solution, the tinted disinfecting solution taken from a class of disinfecting solutions including isopropyl alcohol and chlorhexidine;

the lower chamber below and in fluid connection with the upper chamber, the lower chamber being cylindrical, the lower chamber being transparent, the lower chamber having an upper extent and a lower extent, the lower chamber having an annular ridge projecting radially inward in proximity to the lower conical section of the upper chamber, the annular ridge having an interior diameter, the lower chamber having an interior surface, the interior surface of the lower extent of the lower chamber being formed with female threads, the lower extent of the lower chamber adapted to receive a needleless IV connector port, the lower chamber having a lower end, the lower end of the lower chamber being open, a removable seal covering the open end of the lower end of the lower chamber, the lower chamber having an upper edge and a lower edge;

a wicking material is formed as a cylindrical sponge that extends from the bottom of the lower chamber to the top of the upper chamber and has an external diameter equal to the interior diameter of the annular ridge of the lower chamber, the annular ridge holding the lower end of the sponge in place, a secondary retaining ridge extends downward from the interior bottom surface of the top of the upper chamber having a diameter equal to the interior diameter of the annular ridge; and the removable seal of the lower edge removable for use before removably coupling to the needleless IV connecter port, the lower chamber in fluid connection with the top of the needleless IV connecter port when coupled allowing disinfecting fluid to contact the top of the needleless IV connecter port.

* * * * *